(12) United States Patent
Kwak

(10) Patent No.: US 10,307,097 B2
(45) Date of Patent: *Jun. 4, 2019

(54) METHOD AND SYSTEM FOR SEARCH/TREATMENT OF TINNITUS

(75) Inventor: Sangyeop Kwak, Seoul (KR)

(73) Assignee: Earlogic Korea, Inc., Seoul (KR)

( * ) Notice: Subject to any disclaimer, the term of this patent is extended or adjusted under 35 U.S.C. 154(b) by 1152 days.

This patent is subject to a terminal disclaimer.

(21) Appl. No.: 12/934,330

(22) PCT Filed: May 23, 2008

(86) PCT No.: PCT/KR2008/002910
§ 371 (c)(1),
(2), (4) Date: Dec. 13, 2010

(87) PCT Pub. No.: WO2009/119941
PCT Pub. Date: Oct. 1, 2009

(65) Prior Publication Data
US 2011/0263926 A1  Oct. 27, 2011

(30) Foreign Application Priority Data

Mar. 25, 2008 (KR) ........................ 10-2008-0027222

(51) Int. Cl.
*A61B 5/12* (2006.01)
*A61B 5/00* (2006.01)
*A61F 11/00* (2006.01)
*H04R 25/00* (2006.01)

(52) U.S. Cl.
CPC .............. *A61B 5/411* (2013.01); *A61B 5/121* (2013.01); *A61B 5/128* (2013.01); *A61F 11/00* (2013.01); *H04R 25/50* (2013.01); *A61B 5/0002* (2013.01)

(58) Field of Classification Search
CPC .............................. A61B 5/128; A61B 5/7435
USPC ......................................................... 600/559
See application file for complete search history.

(56) References Cited

U.S. PATENT DOCUMENTS

| | | | |
|---|---|---|---|
| 5,795,287 A | 8/1998 | Ball et al. | |
| 6,155,971 A * | 12/2000 | Calhoun et al. | ................ 600/28 |
| 6,210,321 B1 | 4/2001 | Di Mino et al. | |
| 2004/0131200 A1 | 7/2004 | Davis | |

(Continued)

OTHER PUBLICATIONS

Durst, Chris. "Trouble-shooting cochlear implants day-to-day management, including FM Systems". Presented Feb. 27, 2008. Accessed Aug. 24, 2015 at www.ssc.education.ed.ac.uk/courses/deaf/dfeb08i.html.*

(Continued)

*Primary Examiner* — Rene T Towa
*Assistant Examiner* — H. Q. Nguyen
(74) *Attorney, Agent, or Firm* — Mintz Levin Cohn Ferris Glovsky and Popeo, P.C.; Kongsik Kim; Jhongwoo Jay Peck

(57) ABSTRACT

A method and a system for search/treatment of tinnitus are disclosed. The method includes outputting a tinnitus search interface, which comprises several response regions corresponding to the different frequency bands within audible frequency range of human beings, outputting an acoustic signal corresponding to the response region selected by a user, and storing the frequency information corresponding to the user's tinnitus frequency as a tinnitus frequency band. Accordingly, tinnitus may be rapidly diagnosed and treated.

8 Claims, 6 Drawing Sheets

(56) References Cited

U.S. PATENT DOCUMENTS

2007/0093733 A1* 4/2007 Choy .................... 601/84
2008/0040693 A1* 2/2008 Toyama ............ G06F 9/4446
                                                715/865
2010/0016755 A1* 1/2010 Henry et al. ............ 600/559

OTHER PUBLICATIONS

International Search Report for International Patent Application No. PCT/KR2008/02910.

* cited by examiner

[Fig. 1]
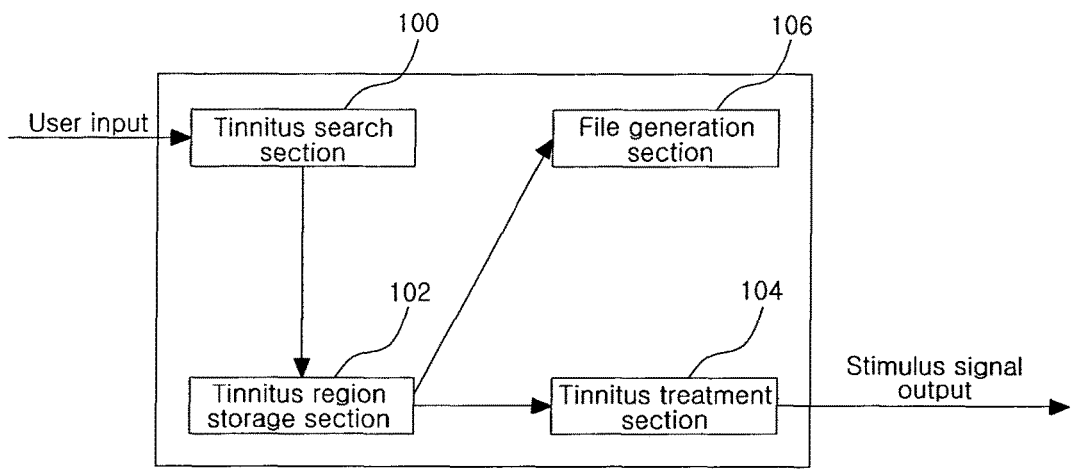
[Fig. 2]
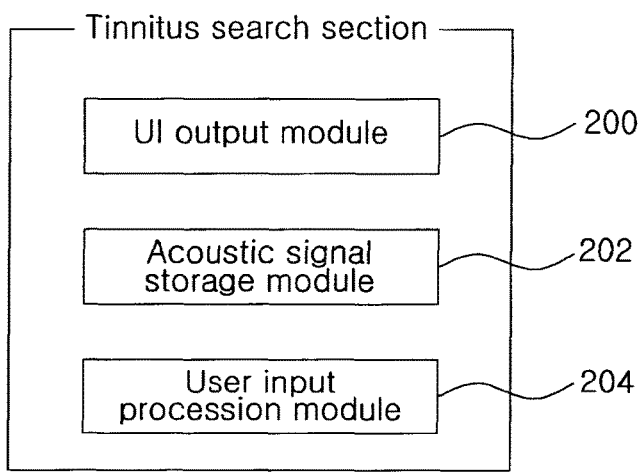

[Fig. 3]
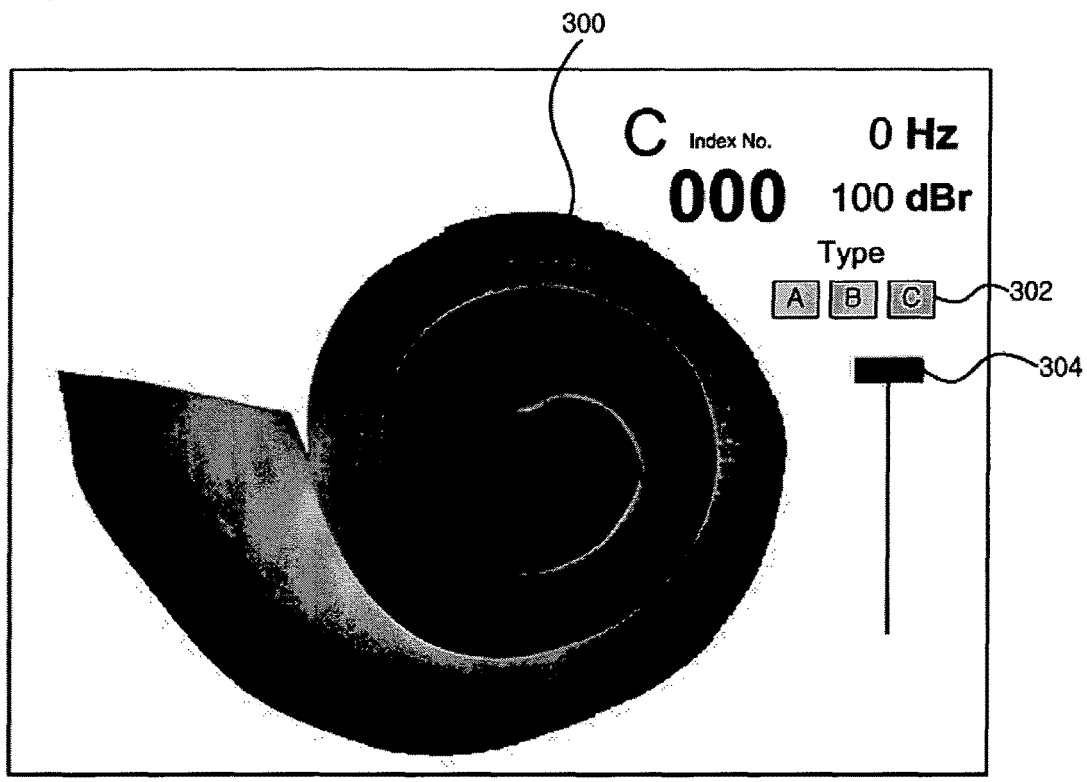
[Fig. 4]
| Index No | Frequency(Hz) |
|---|---|
| 1 | 254 |
| 2 | 262 |
| ⋮ | ⋮ |
| 134 | 11840 |

[Fig. 5]
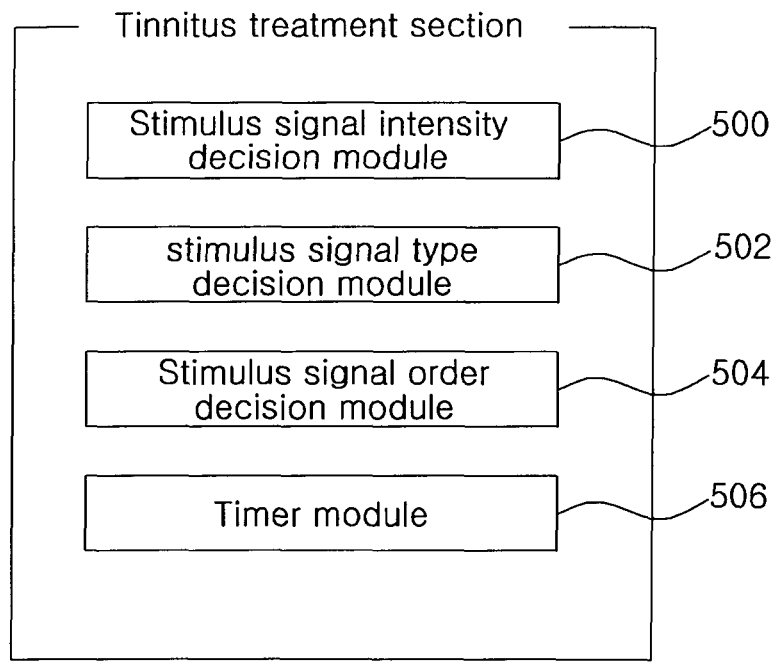

[Fig. 6]
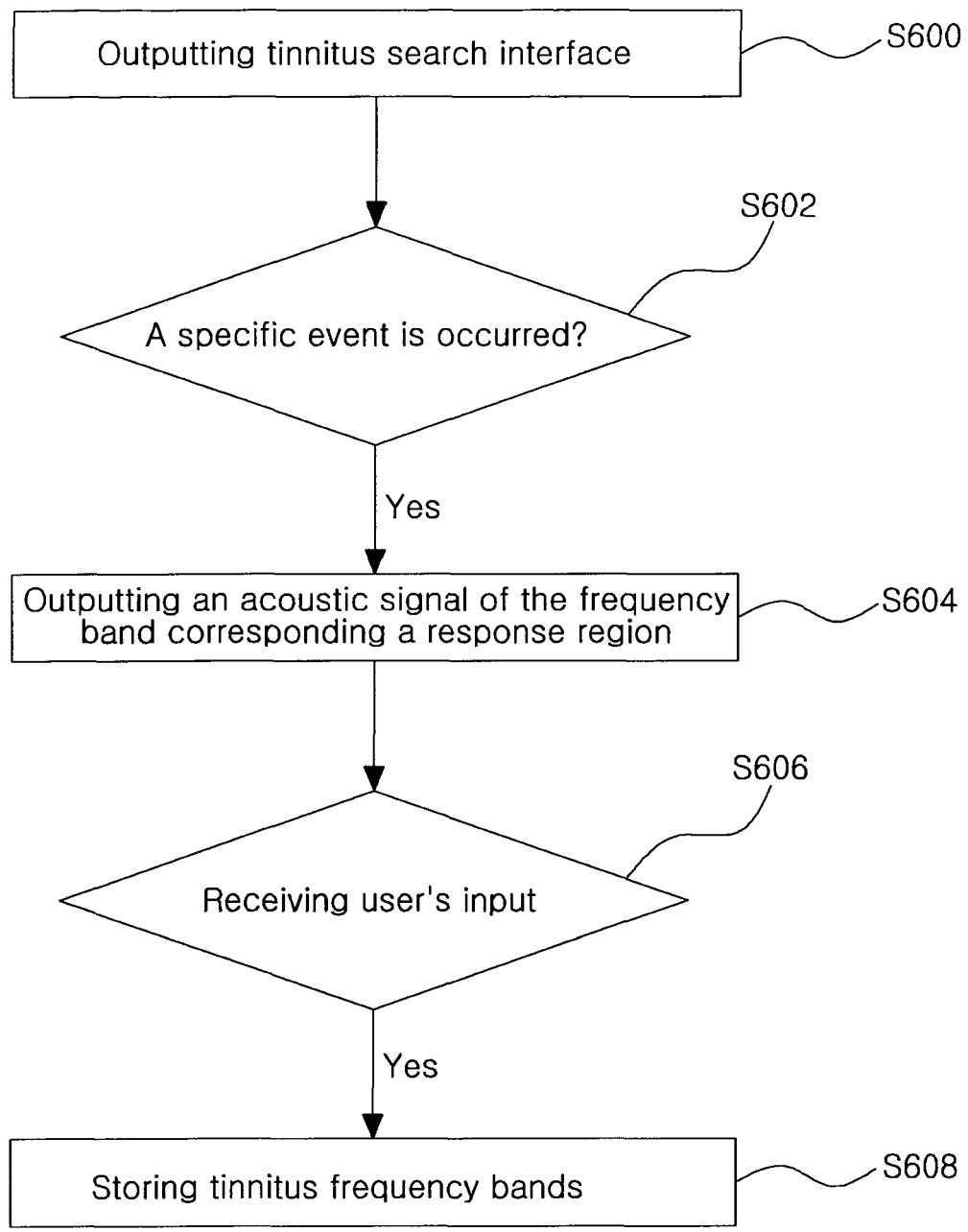

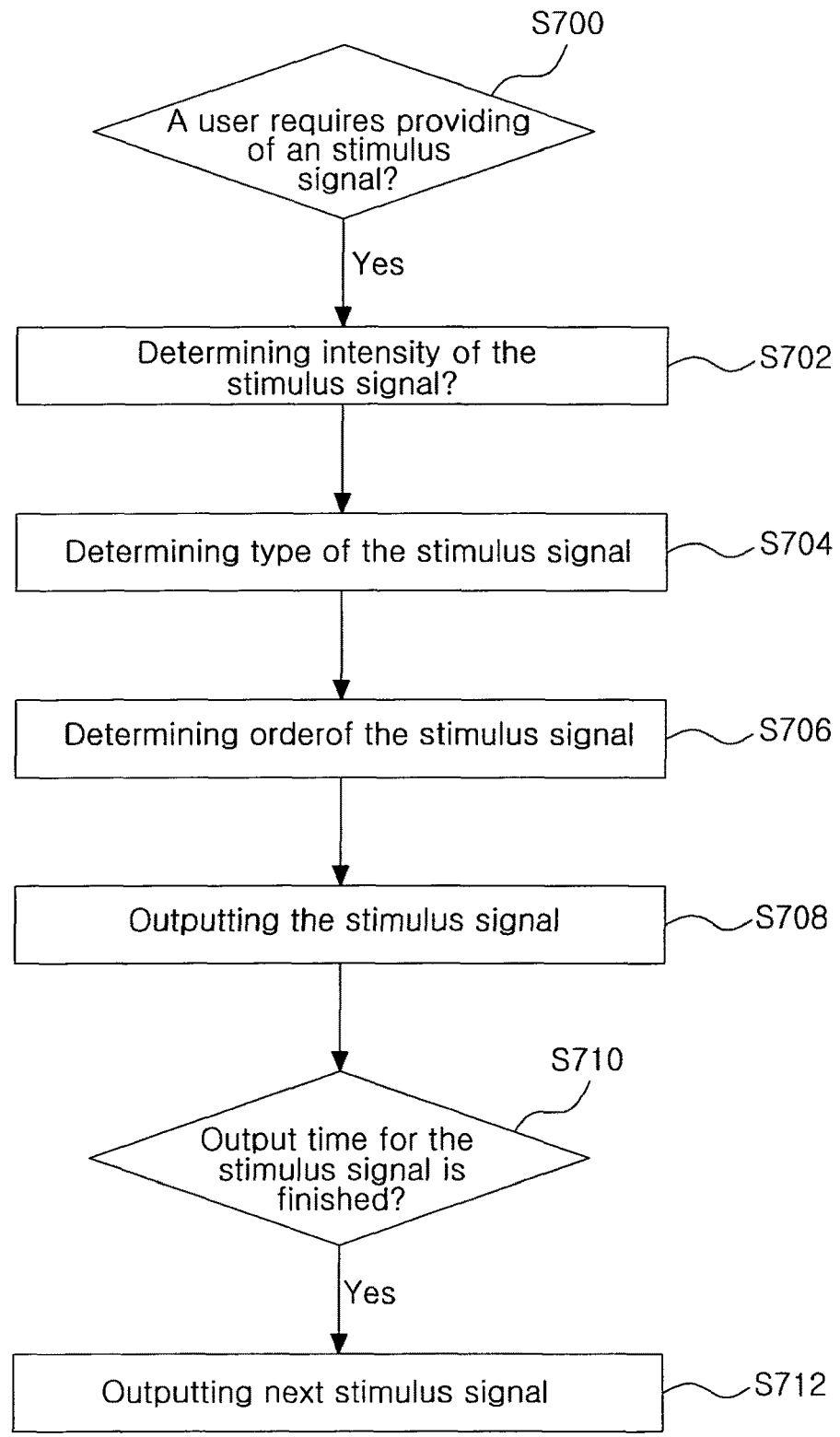
[Fig. 7]

[Fig. 8]
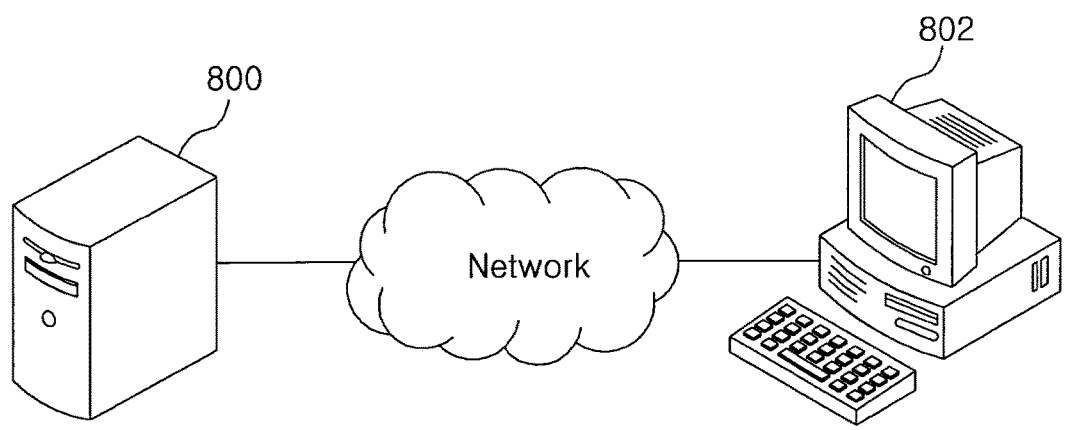

METHOD AND SYSTEM FOR SEARCH/TREATMENT OF TINNITUS

TECHNICAL FIELD

Example embodiment of the present invention relates to a method and a system for search/treatment of tinnitus. More particularly, the present invention relates to a method and a system for easily searching tinnitus frequency regions of a user and effectively treating the tinnitus.

BACKGROUND ART

Tinnitus is defined as the perception of sound by an individual when no external sound is present, which is resulted from damage of hair cells in the inner ear or other various diseases.

Currently, 85% of tinnitus are known to be involved in the hair cell damage, which is resulted from traumatic noise, aging, side effects of specific drugs, allergy, inflammation of the outer or middle ear.

Since tinnitus affects daily life as well as mental health of a patient who is suffering from tinnitus, the patient seeks medical intervention including effective treatment. However, in many cases, it is difficult to find out the cause of tinnitus and to treat the tinnitus. Especially, in case of tinnitus caused by hair cell damage, it is more difficult.

In general, tinnitus is diagnosed by subjective judgment of the tinnitus patient, and among the treatment methods are pharmacological treatment, surgery, masking method, and TRT (tinnitus retraining treatment).

In the pharmacological treatment, the drugs for tinnitus treatment could affect neural response of central nervous system or cochlear response in direct/indirect manner. In addition, the drugs can induce some degree of drug tolerance like antidepressants.

Although some drugs such as tranquilizers, antidepressants, and sedatives are known to reduce the severity of tinnitus, the drugs can cause unwanted side effects.

Surgical treatment has a limit on its application because it is performed only for the tinnitus resulted from an abnormality of brain blood system.

Tinnitus masking method uses a noise generator to produce a masking noise, which comprises the same frequency signal as a patient's tinnitus sound and prevents a tinnitus patient from detecting his/her own tinnitus sound.

Tinnitus retraining treatment is a method for habituation of tinnitus and helps a patient to be able to unconsciously ignore the tinnitus sound.

Although both masking method and tinnitus retraining treatment are trying to apply the same signal as patient's tinnitus, in most cases, theses methods fail to accurately diagnose the frequency regions of tinnitus. The reason is that the methods use low-resolution signals that are divided by more than one octave resolution. In addition, the methods take very long time to search the tinnitus frequency region because the diagnosis process including both signal presentation by a specialist and response of a patient should be repeated several times.

Especially, since the masking method should be applied whenever a tinnitus patient detects tinnitus sound, the method is a kind of temporal alternative rather than treatment method.

Additionally, tinnitus retraining treatment may cause damage to the normal hearing region since this method should apply a wide range of noise to the auditory system as long as the low-resolution signals are used for the tinnitus diagnosis.

DISCLOSURE

Technical Problem

Accordingly, the present invention is provided to substantially obviate one or more problems due to limitations and disadvantages of the related art.

It is a feature of the present invention to provide a method and a system for search/treatment of tinnitus for more accurately and rapidly diagnosing the tinnitus frequency regions.

It is another feature of the present invention to provide to a method and a system for search/treatment of tinnitus so as to fundamentally treat the tinnitus.

Technical Solution

A method for search/treatment of tinnitus according to one example embodiment of the present invention includes (a) outputting a tinnitus search interface, which comprises several response regions corresponding to different frequency bands within audible frequency range of human beings; (b) outputting an acoustic signal corresponding to the response region selected by a user; and (c) storing the frequency information of an acoustic signal corresponding to the tinnitus frequency of a user as a tinnitus frequency band.

A method for search/treatment of tinnitus according to another example embodiment of the present invention includes (a) searching tinnitus frequency bands by using acoustic signals generated by dividing audible frequency range of human beings with 1/k octave resolution, wherein the k is positive integer above 2 and the acoustic signals are different from each other in their frequency bands; and (b) outputting a stimulus signal of a predetermined intensity to the same frequency band as the one searched above.

A recording media having program for performing the above methods and read by a computer is provided.

A method of providing a tinnitus search/treatment service in a server connected electrically to a client through a network according to one example embodiment of the present invention includes (a) transmitting a tinnitus search interface to the client, wherein the tinnitus search interface comprises several response regions corresponding to the different frequency bands within audible frequency range of human beings and outputs an acoustic signal corresponding to the response region selected by a user; (b) receiving user's input information; and (c) storing the frequency information corresponding to the tinnitus frequency of a user as a tinnitus frequency band.

Advantageous Effects

As described above, in a method and a system for search/treatment of tinnitus, a user may accurately and rapidly diagnose the tinnitus frequency regions by using acoustic signals divided with high-resolution.

In a method and a system for search/treatment of tinnitus, various types of acoustic signals are provided. Therefore, a user may accurately diagnose tinnitus by using the various types of acoustic signals.

A method and a system for search/treatment of tinnitus may effectively treat tinnitus by providing stimulus signal corresponding to finely divided-frequency bands.

DESCRIPTION OF DRAWINGS

Example embodiments of the present invention will become more apparent by describing in detail example embodiments of the present invention with reference to the accompanying drawings, in which:

FIG. 1 is a block diagram illustrating an apparatus for search/treatment of tinnitus according to one example embodiment of the present invention.

FIG. 2 is a block diagram illustrating detail composition of a tinnitus search section according to one example embodiment of the present invention.

FIG. 3 is a view illustrating a tinnitus search interface according to one example embodiment of the present invention.

FIG. 4 is a view illustrating a storage table indicating frequency bands of acoustic signals according to one example embodiment of the present invention.

FIG. 5 is a block diagram illustrating detail composition of a tinnitus treatment section according to one example embodiment of the present invention.

FIG. 6 is a flow chart illustrating a process of tinnitus search according to one example embodiment of the present invention.

FIG. 7 is a flow chart illustrating a process of tinnitus treatment according to one example embodiment of the present invention.

FIG. 8 is a view illustrating a service system for tinnitus search/treatment according to another example embodiment of the present invention.

MODE FOR INVENTION

Example embodiments of the present invention are disclosed herein. However, specific structural and functional details disclosed herein are merely representative for purposes of describing example embodiments of the present invention. Example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise", "comprising,", "include" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram illustrating rough composition of an apparatus for search/treatment of tinnitus according to one example embodiment of the present invention.

In FIG. 1, the apparatus for search/treatment of tinnitus of the present embodiment includes a tinnitus search section 100, a tinnitus region storage section 102, a tinnitus treatment section 104, and a file generation section 106.

The tinnitus search section 100 outputs an interface and an acoustic signal for searching the tinnitus frequency bands of a user (a subject).

FIG. 2 is a block diagram illustrating detail composition of a tinnitus search section 100 according to one example embodiment of the present invention.

The tinnitus search section 100 of the present embodiment includes a UI (User Interface) output module 200, an acoustic signal storage module 202, and a user input processing module 204.

The UI (User Interface) output module 200 outputs a tinnitus search interface, which makes it possible to easily and rapidly search tinnitus frequency bands.

The tinnitus search interface of the present embodiment includes a response region, in which an acoustic signal of the selected frequency band is outputted when a user selects.

In one example embodiment of the present invention, the tinnitus search interface displays a cochlear model interface and includes an image (hereinafter, referred to as auditory hair cell region image, 300) corresponding to each auditory hair cell region with frequency specificity within the audible frequency range of human beings (e.g. 250~12000 Hz).

The auditory hair cell region image 300 includes several hair cell region images.

In one example embodiment of the present invention, when a specific event (location of a mouse cursor or user's touch) occurs on the auditory hair cell image, an acoustic signal of the frequency band corresponding to the position is outputted.

That is, the auditory hair cell image shown in FIG. 3 is also a response region.

In addition, the tinnitus search interface includes a signal type decision part 302 and a volume adjustment part 304.

In one example embodiment of the present invention, an acoustic signal, which is generated by dividing audible frequency range of human with high resolution, is provided to search tinnitus frequency bands.

Preferably, the acoustic signal divided with 1/k (is positive integer above 2) octave resolution, more preferably, 1/3 to 1/24 octave resolution is provided.

The acoustic signal storage module 202 stores an index table about frequency bands finely divided with high resolution.

In case that the acoustic signal is divided with 1/24 octave resolution, the audible frequency range is divided to 134 bands. As shown in FIG. 4, the acoustic signal storage module 202 matches the index number and the center frequency of each frequency band and stores the matching result.

In one example embodiment of the present invention, the index number is matched to each response region of the tinnitus search interface. Therefore, in case that a user selects number 1 response region, an acoustic signal with 254 Hz center frequency, which is matched to index number 1, is outputted. In case that a user selects number 2 response region, an acoustic signal with 262 Hz center frequency, which is matched to index number 2, is outputted. In case that a user selects number 134 response region, an acoustic signal with 11840 Hz center frequency, which is matched to index number 134, is outputted.

Since the tone of tinnitus is various depending on a subject, the type of an acoustic signal of the present embodiment includes at least one of pure tone and narrow band or combination of pure tone and narrow band noise. A user can select the type of an acoustic signal before outputting the acoustic signal.

The user input processing module 204 discriminates whether or not a specific event occurs on the tinnitus search interface. In case that the specific event is detected on a response region, the user input processing module 204 executes the corresponding procedure.

In one example embodiment of the present invention, the user input processing module 204 discriminates specific events such as the location of mouse cursor on each response region or user's touch.

In addition, the user input processing module 204 receives the information about the acoustic signal type and volume level selected by a user and executes the procedure corresponding to the received information.

Only with moving the mouse on the tinnitus search interface shown in FIG. 3, a user can hear the acoustic signal corresponding to the specific frequency band and search the same acoustic signal as the user's tinnitus sound.

The tinnitus region storage section 102 stores the frequency band of the acoustic signal corresponding to the tinnitus frequency of a user as a tinnitus frequency band. The corresponding tinnitus frequency band may be stored as a center frequency as shown in FIG. 4. Here, the tinnitus region storage section 102 stores one or more than one of tinnitus frequency bands because the number of the tinnitus frequency band is one or more than one.

Since tinnitus search is determined by user's subjectivity, storage of tinnitus frequency bands is performed in case that a user inputs the index number corresponding to the user's tinnitus frequency or that there is a user's inputs while the user is listening to an acoustic signal corresponding to a certain response region.

The tinnitus treatment section 104 outputs a stimulus signal of a predetermined intensity (dB) to the tinnitus frequency band. Here, the intensity of the stimulus signal has no limitation as long as the signal stimulates damaged auditory hair cells. Preferably, the stimulus signal is a sound signal for stimulating auditory hair cell and the intensity of the stimulus signal may be below 5 dBSL (sensational level).

In one example embodiment of the present invention, the stimulus signal corresponds to at least one of amplitude modulated tone, frequency modulated tone, pulse tone and amplitude modulated narrowband noise, or combination of the tones and the noise.

Furthermore, in case that several hair cell regions need stimulation, that is, in case that several tinnitus frequency bands are determined, the stimulus signals are provided to the tinnitus frequency bands in an order of frequency or randomly. However, the presentation of the stimulus signals is not limited as the above method. For example, stimulus signals corresponding to several tinnitus frequency bands may be simultaneously provided to stimulate several auditory hair cells at the same time.

In case that the stimulus signals of various intensities, types or orders are provided to the auditory hair cells generating tinnitus of a user, the tinnitus of the user may be effectively improved.

FIG. 5 is a block diagram illustrating detail composition of a tinnitus treatment section 104 according to one example embodiment of the present invention.

As shown in FIG. 5, the tinnitus treatment section 104 of the present embodiment includes a stimulus signal intensity decision module 500, a stimulus signal type decision module 502, a stimulus signal order decision module 504, and a timer module 506.

The stimulus signal intensity decision module 500 determines the intensity of stimulus signal being provided to a user.

The stimulus signal type decision module 502 determines the type of stimulus signal based on a user's selection, a user's tinnitus frequency band requiring treatment, or a signal type selected for search of tinnitus frequency bands.

As mentioned above, components of stimulus signal include amplitude modulated tone, frequency modulated tone, continuous tone, pulse tone and amplitude modulated narrowband noise. The stimulus signal type decision module 502 determines at least one or combination of the above components as the stimulus signal type being provided to a user.

The stimulus signal order decision module 504 determines stimulus signal output order about several tinnitus frequency bands based on a user's selection, user's tinnitus frequency bands requiring treatment, or a signal type selected for search of tinnitus frequency bands.

Preferably, the stimulus signal order decision module 504 of the present embodiment may determine the output order so that the stimulus signal is outputted in sequence from the low tinnitus frequency band to the high tinnitus frequency band, or in the opposite sequence. However, the above output order is not limited as the order mentioned above. For example, the stimulus signals may be randomly outputted, or be simultaneously outputted to the several tinnitus frequency bands.

In case that the stimulus signal of the intensity, type, and output order determined as mentioned above is outputted, output time of the stimulus signal may be set. After discriminating whether stimulus signal output time is completed or not, the timer module 506 commands to output a stimulus signal corresponding to the next tinnitus frequency band or to complete the stimulus signal output.

While the stimulus signal is outputted, the UI (User Interface) output module 200 displays information about the stimulus signal on the tinnitus search interface shown in FIG. 3, wherein the user visually recognizes the presence or absence, intensity, type, etc of the stimulus signal through the information.

For example, the UI (User Interface) output module 200 may change color or size of the auditory hair cell region image 300 corresponding to the tinnitus frequency band of the stimulus signal outputted now.

In case that the stimulus signal is the amplitude modulated tone, the UI (User Interface) output module 200 may change color or size of the corresponding auditory hair cell region image 300 synchronizing with amplitude change of the amplitude modulated tone.

In case that the stimulus signal is the frequency modulated tone, the UI (User Interface) output module 200 may change color or size of the auditory hair cell region image 300 corresponding to the changed frequency synchronizing with frequency change of the frequency modulated tone.

In case that the stimulus signal is the continuous tone or the pulse tone, the UI (User Interface) output module 200 may change color or size of the corresponding auditory hair cell region image 300 so that the user recognizes the currently provided stimulus signal as the continuous tone or the pulse tone.

FIG. 1 may be an application for searching and storing the user's tinnitus frequency band and for providing a stimulus signal corresponding to the user's tinnitus frequency band.

Since this application is performed by a user's computer at home or office, the stimulus signal is provided to the user only at home or office.

To provide a stimulus signal without temporal or spatial limitation after the search of tinnitus is finished, the apparatus for search/treatment of tinnitus according to one example embodiment of the present invention may include a file generation section 106 shown in FIG. 1. Wherein, the file generation section 106 generates a preset stimulus signal file based on the information about a tinnitus frequency band.

The file generation section 106 generates a stimulus signal as a format which is played in portable devices such as an MP3 player or a portable terminal.

Accordingly, the file generation section 106 may generate the stimulus signal to be provided to a user as an compacted file by interlocking with the tinnitus region storage section 102 and the tinnitus treatment section 104, and transmit the stimulus signal file to a portable device.

Hereinafter, the method for search/treatment of tinnitus will be described in detail with reference to accompanying FIG. 6 or FIG. 7.

FIG. 6 is a flow chart illustrating a process of tinnitus search according to one example embodiment of the present invention.

Referring to FIG. 6, the apparatus for search/treatment of tinnitus outputs a tinnitus search interface comprising a cochlear model on display space in case that a user requests in step S600.

The cochlear model may include auditory hair cell images. Here, the auditory hair cell image makes it possible to visually discriminate frequency bands which are generated by dividing middle-frequency region with a maximum $1/24$ octave-high resolution.

Here, the auditory hair cell image corresponds to the response region outputting an acoustic signal when a specific event occurs.

In step S602, the apparatus for search/treatment of tinnitus discriminates whether or not a specific event occurs on the response region mentioned above.

In step S604, in case that a specific event (location of a mouse cursor or user's touch) is detected on the response region, an acoustic signal of the frequency band corresponding to the response region is outputted.

Before the acoustic signal is outputted, a user may select the volume or type of the acoustic signal and the acoustic signal of selected volume and type is outputted.

Here, the center frequency and the index number of the acoustic signal may be displayed together by using the pre-stored information.

In step S606, the apparatus of search/treatment of tinnitus discriminates whether or not there is a specific input by the user listening to the acoustic signal.

In step S608, in case that there is user's input or input of index number while the user is listening to the acoustic signal of the frequency band corresponding to a specific response region, the apparatus of search/treatment of tinnitus stores the corresponding response region or the frequency band of the index number as the user's tinnitus frequency band.

In step S608, several tinnitus frequency bands of a user may be stored.

FIG. 7 is a flow chart illustrating a process of tinnitus treatment according to one example embodiment of the present invention.

Referring to FIG. 7, in step S702, the apparatus for search/treatment of tinnitus determines the intensity of a stimulus signal corresponding to the user's tinnitus frequency band stored in step S608 in case that the user requests providing of the stimulus signal in step S700.

In accordance with step S702, the type and output order of the stimulus signal is determined in step S704 and step S706, respectively.

As mentioned previously, in case that several tinnitus frequency bands are present, the output order of the stimulus signals is determined in sequence from the low tinnitus frequency band to the high tinnitus frequency band, or in the opposite sequence. In addition, the stimulus signals may be randomly outputted, or be simultaneously outputted.

In step S708, the stimulus signal is outputted in accordance with the determined intensity, type, and order.

In step S710, in case that the stimulus signal is outputted randomly or in an order, the apparatus for search/treatment of tinnitus of the present embodiment determines whether or not stimulus signal output time is completed.

In step S712, in case that the output time is completed, a stimulus signal of next tinnitus frequency band is outputted.

On the other hand, in case that the stimulus signal is outputted, the apparatus for search/treatment of tinnitus synchronizes the tinnitus search interface with the presence or absence of a stimulus signal, amplitude change, frequency change or pulse period of the stimulus signal, and changes color or size of the auditory hair cell region image 300 of the tinnitus search interface in accordance with the synchronization.

The service for search/treatment of tinnitus of the present embodiment is provided through a computer or a portable terminal established by the user or in a hospital, etc. In addition, the service may be provided through a network at a remote place.

FIG. 8 is a view illustrating a service system for search/treatment of tinnitus according to one example embodiment of the present invention.

In FIG. 8, the service system for search/treatment of tinnitus of the present embodiment includes a service server 800 connected electrically to at least one user client 802 through a network. Here, the network includes a wire network having an Internet and a private line and a wireless network having a wireless Internet, a mobile communication network, and a satellite network.

In case that a user requests, the service server 800 provides an application for outputting a tinnitus search interface comprising a cochlear model shown in FIG. 3 and for outputting a stimulus signal selected by the user to the user client 802. Here, the service server 800 may provide the application through various methods such as a download, webpage-inserted form, etc.

The application performed in the user client 802 outputs a tinnitus search interface including a tinnitus search module shown in FIG. 1 or FIG. 2. In addition, in case that a specific event occurs on a response region 300 corresponding to an auditory hair cell image, the application outputs the stimulus signal corresponding to the response region where the specific event occurs.

In case that the tinnitus search/treatment service is provided through a network shown in FIG. 8, the application transmits the user's input information about tinnitus frequency bands to the service server 800.

After receiving the user's input information, the service server 800 stores the frequency bands included in the input information as the user's tinnitus frequency bands.

On the other hand, in case that a user requests, the service server 800 transmits the information related to a stimulus signal for treatment of the user's tinnitus to the user client 802. Here, the information related to the stimulus signal may include the pre-stored information about the user's tinnitus frequency band and the information about the intensity, type and order of the stimulus signal.

The application installed in the user client 802 outputs the stimulus signal of the intensity, type and order determined by using the above information related to the stimulus signal.

On the other hand, in case that a user requests, the service server 800 may not provide the stimulus signal in real-time and generate a separate stimulus signal file corresponding to the user's tinnitus frequency band.

The stimulus signal files may be transmitted to a user's mobile device through a download method. Therefore, the user may be provided with the stimulus signal for tinnitus treatment without temporal or spatial limitations.

In the above embodiment of the present invention, the application outputs only the user interface and the acoustic signal, and the service server 800 is in charge of storing the tinnitus frequency band and providing the stimulus signal for tinnitus treatment. However, the above embodiment is no more than one example, and it will be apparent to those skilled in the art that the application may perform the all processes.

INDUSTRIAL APPLICABILITY

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A method for searching and treating tinntus of a user, the method comprising:

displaying, by a tinnitus search program executing on a service server or a user client, a cochlear model user interface that comprises an interactive cochlear image comprising a plurality of response regions corresponding to auditory hair cell regions that respond to different frequency bands within an audible frequency range of human beings, wherein the response regions are provided in a number obtained by dividing the audible frequency range of human beings with 1/k octave resolution, having k as a positive integer within a range of 3 to 24;

outputting, by the tinnitus search program, an acoustic signal corresponding to a response region as the user selects the response region from the plurality of response regions;

providing, by the tinnitus search program, a visual response in the response region selected by the user, wherein the visual response includes at least one from a group consisting of a size change of the selected response region of the cochlear image, a color change of the selected response region of the cochlear image, and a geometry change of the selected response region of the cochlear image;

receiving by a user input processing module of the tinnitus search program, an input from the user designating a frequency band of the acoustic signal corresponding to the selected response region as a tinnitus frequency band of the user;

storing, by a tinnitus region storage program executing on the service server or the user client, frequency information of the acoustic signal corresponding to the tinnitus frequency band of the user; and outputting, by a tinnitus treatment program executing on the service server or the user client, a stimulus signal for treating tinnitus having a predetermined intensity at the tinnitus frequency band of the user, the stimulus signal including at least one of an amplitude modulated tone, a frequency modulated tone, a pulse tone, and an amplitude modulated narrowband noise, wherein the cochlear model user interface visually notifies the user a presence, intensity and type of the stimulus signal, wherein, when the stimulus signal for treating tinnitus includes a plurality of frequency bands, the tinnitus treatment program outputs the plurality of frequency bands simultaneously or randomly.

2. The method of claim 1, wherein the acoustic signal is outputted by the tinnitus search program when a specific event occurs in the selected response region.

3. The method of claim 1, wherein the acoustic signal corresponds to a pure tone, narrow band noise, or a combination thereof.

4. The method of claim 1, wherein, when the stimulus signal for treating tinnitus includes the amplitude modulated tone, an amplitude variation of the amplitude modulated tone is visualized by a change in the selected response region of the cochlear image.

5. The method of claim 1, wherein, when the stimulus signal for treating tinnitus includes the frequency modulated tone, a frequency variation of the frequency modulated tone is visualized by a change in the selected response region of the cochlear image.

6. The method of claim 5, wherein the frequency modulated tone has a resolution less than ⅓ octave.

7. The method of claim 1, wherein, when the stimulus signal for treating tinnitus includes one of a continuous tone or a pulse tone, whether the stimulus signal corresponds to the continuous tone or the pulse tone is visualized by the selected response region of the cochlear image.

8. The method of claim 1, further comprising:
generating, by a file generation program executing on the service server or the user client, a preset file format of the stimulus signal for treating tinnitus corresponding to the tinnitus frequency band of the user.

* * * * *